United States Patent [19]
Pernot

[11] Patent Number: 5,090,906
[45] Date of Patent: Feb. 25, 1992

[54] PUSH-BUTTON CONTROL DEVICE FOR A DENTAL INSTRUMENT

[75] Inventor: Jacques Pernot, Geneville, France

[73] Assignee: Micro Mega SA, Besancon, France

[21] Appl. No.: 578,546

[22] Filed: Sep. 6, 1990

[30] Foreign Application Priority Data

Sep. 7, 1989 [FR] France ............... 89 11866
Sep. 8, 1989 [FR] France ............... 89 11945
Nov. 23, 1989 [FR] France ............... 89 15596

[51] Int. Cl.⁵ ............................ A61C 1/14; A61C 1/08
[52] U.S. Cl. ............................ 433/127; 433/126; 433/128
[58] Field of Search ............... 433/126, 127, 129

[56] References Cited

U.S. PATENT DOCUMENTS

4,536,157 8/1985 Maizenberg ............... 433/129
4,595,363 6/1986 Nakanishi ............... 433/129
4,611,990 9/1986 Lares et al. ............... 433/129
4,874,314 10/1989 Fleer et al. ............... 433/129

*Primary Examiner*—John J. Wilson
*Assistant Examiner*—Cindy A. Cherichetti
*Attorney, Agent, or Firm*—Weiser & Stapler

[57] ABSTRACT

The cutting shank of an instrument to be received in the head of a contra-angle of a dentistry handpiece is clamped in position with a pushed-button control device which is displacable counter to a tensioning spring. The control device generally takes the form of at least one reversal element for receiving pressures responsive to movements of the push-button and for converting such movements into a traction movement exerted by the reversal element on the pusher which is used to control the collet chuck which receives the shank of the instrument.

33 Claims, 5 Drawing Sheets

PUSH-BUTTON CONTROL DEVICE FOR A DENTAL INSTRUMENT

The present invention relates to a push-button control device for clamping and, respectively, unclamping the cutting shank of a dentistry instrument in the head of a contra-angle or a handpiece, the displacement of the push-button being effected counter to a pressure spring.

In the generally known devices, one or more springs ensure the sustaining of the clamping. The unclamping is permitted by the pressure or the release of the said spring by virtue of the downward movement of one of the ends of the spring, and this by way of various mechanical elements. This downward movement is in the same direction as that imparted to the press-button for controlling the unclamping.

The following problems result from this:

it is impractical to ensure a demultiplication so that the force to be exerted on the button is reduced, and this leads to the adopting of a compromise in the choice of the spring for maintaining clamping, which does not permit a great clamping force;

the travel of the push-button in the unclamping action is in direct relation with that of the clamping elements; it is thus in general short and this is not favourable to a good sensitivity of action of the operation and constitutes a risk factor involving accidental unclamping due to a slight action on the pushbutton.

The aim of the invention is to overcome these disadvantages of the devices of the prior art by proposing a device permitting a significant travel of the push-button, a demultiplication of the force and, finally a clamping device which is all the more effective as a traction force is exerted on the instrument.

According to the invention, this result is achieved with a push-button control device for clamping and, respectively, unclamping the cutting shank or a dentistry instrument in the head of a contra-angle of a handpiece, the displacement of the push-button being effected counter to a pressure spring, characterized in that it comprises at least one reversal element receiving the movement of pressing on the push-button for the unclamping and converting it into a traction movement exerted by the reversal element on a pusher controlling a collet chuck holding the shank of the instrument.

The said element will advantageously be a lever-type tilting element.

Figure 1:
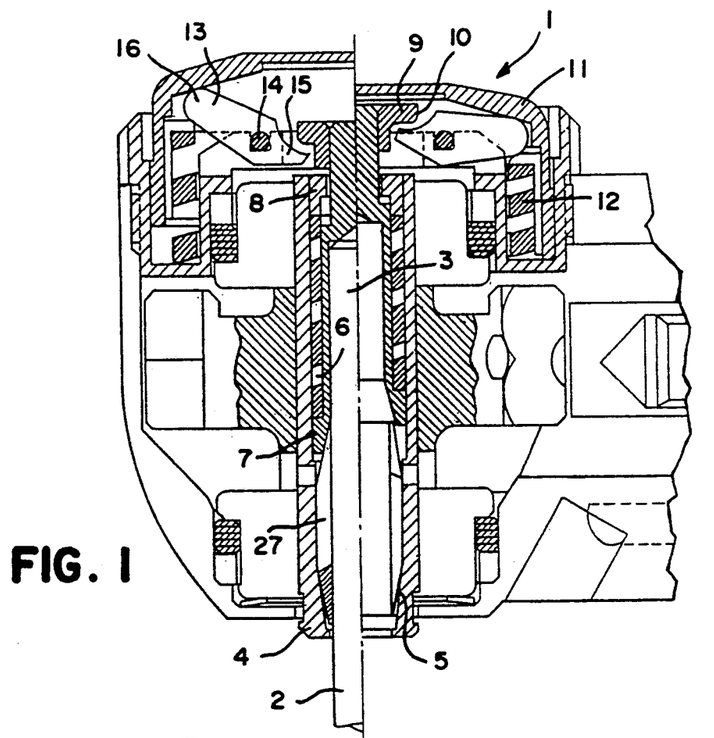
FIG. 1 is a cutaway view of a head comprising a device according to the invention, seen in the clamping position in the left-hand half and seen in the unclamping position in the right-hand half.

Other aims and characteristics of the invention will emerge from the description which is given hereinbelow of a number of examples of implementation given as non-limiting examples, and in which reference is made to the attached drawings in which:

FIGS. 8 to 11 and 8A to 11A are four other variants of implementation in a representation identical to that in FIG. 7, with in addition cutaways along B—B represented in FIGS. 10B and 11B;

FIG. 1 represents a contra-angle head designated by reference (1) and designed to receive a dentistry instrument (2) whose shank (3) is inserted in a shaft (4) of the said head (1).

The neck is held by a collet chuck (5) stressed by a pressure spring (6), for example helical, which bears on the one hand on a movable base (7) and on the other hand on a seat (8).

According to the invention, a movable annular piece (9) is provided in the head, the said piece comprising a shoulder of the pusher (10) and being integral in translation with the base (7). It will be understood that the axial displacement of the equipment (7, 9, 10) results in the compression or the release of the spring, hence the freeing or blocking of the neck of the instrument which is held by the chuck (5).

The displacement of the assembly (7, 9, 10) is controlled by a push-button (11) which is displaced counter to the force of a return spring (12) in the release position.

The link between the button (11) and the assembly (7, 9, 10) is obtained in FIG. 1, by at least one lever (13) articulated on a pin (14). The lever and the demultiplication are such that the displacement of the button is greater relative to the necessary travel of the assembly (7, 9, 10), that is to say the small arm (15) of the lever will act upon the shoulder (10) while the large arm (16) will be subjected to the action of the pushbutton, on the inner face of the latter.

The device will comprise several levers of this type, distributed in a symmetrical manner.

Figure 2:
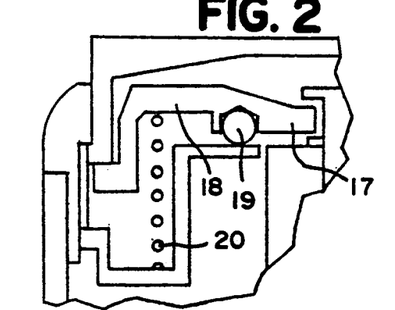
FIG. 2 is a diagrammatic semi-cutaway view of a lever with a fulcrum on a ball.

The device in FIG. 2 is similar, with a small arm (17), a large arm (18) and a fulcrum which is a ball (19). In this design, the spring (20), similar to the spring (12), bears on the large arm (18), the latter itself being acted upon by the push-button.

Figure 3:
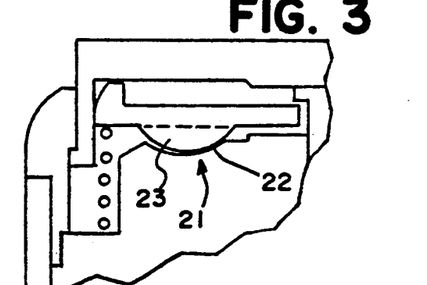
FIG. 3 is a diagrammatic semi-cutaway view of a lever of the boat key type.
Figure 4:
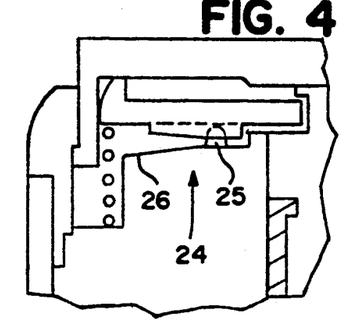
FIG. 4 is a diagrammatic semi-cutaway view of a lever of the balance-arm type.
Figure 5:
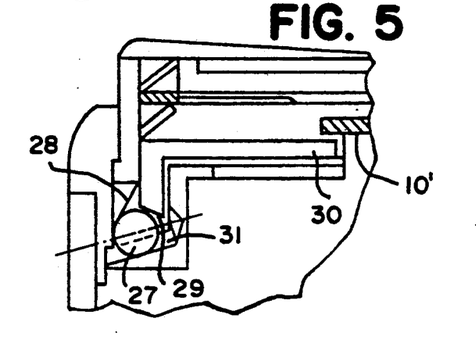
FIG. 5 is a variant with a ball system.

In FIG. 3 the lever is of the boat-shaped key type (21) that is to say comprising a basin (22) in which a ball (23) rolls. The boat keys are preferably extended by an arm ensuring the off-centring of the points of contact relative to the imaginary axis of rotation.

All the other elements are identical to those in the preceding embodiments.

In order to perfect the results thereby obtained, account must be taken of the fact that the high rotational speeds reached at present by dental handpieces necessitate that the moving components be correctly equilibrated, in order to eliminate the risks of wear of the ball bearings, for example.

The device for clamping the instruments is one of the most sensitive elements since, being at the end of the kinematic chain, it turns at the maximum speed. In order to confer upon it good conditions of equilibration, that is to say in order reduce as far as possible the effects of unbalance, it is attempted to give it the lowest possible inertia, which must be reflected in forms of revolution of the lowest possible diameter, while at the same time ensuring adequate clamping of the instrument.

Among the existing devices, that described in the patent application published under U.S. Pat. No. 2,576,775 is known, for example, which has the disadvantage of having movable pieces in respect of which it is impossible to ensure that they systematically recover the same position after each actuation of the device, which results in a risk of losing the conditions of equilibration. A device is also known from U.S. Pat. No. 2,336,593, which device can consist of one or two clamping pieces and which, by virtue of its design, provides for a constant clamping force dependent on the quality of the spring with which it is equipped.

The aim of the invention is to propose a clamping and unclamping device of a form of revolution which affords a high degree of clamping stability and optimal holding at all the rotational speeds, without a risk of wearing of the elements constituting the head of the handpiece.

According to the invention, this result is achieved with a device for clamping and unclamping the shank of a dental instrument in the head of a dentistry handpiece, the device being of the type in which the shank of the instrument is inserted into a shaft inside which it is held by a collet chuck, characterized in that the collet chuck is actuated by a ramp of corresponding shape and integral with a pusher movable in translation inside the shaft and whose displacement is controlled directly or indirectly by a push-button actuated by the user, the pusher being returned by a pressure spring bearing on the one hand on a base integral with the pusher and on the other hand on a fixed seat integral with the shaft.

According to an important characteristic of the invention, the unclamping is effected by means of traction on the pusher of the chuck.

This device affords a high degree of clamping stability to the extent that, when the practitioner operates with traction on the instrument, the clamping force increases with the traction force, thereby preventing any risk of losing the instrument in the mouth of the patient.

Of course, the control push-button will be of the type described previously.

Figure 6:
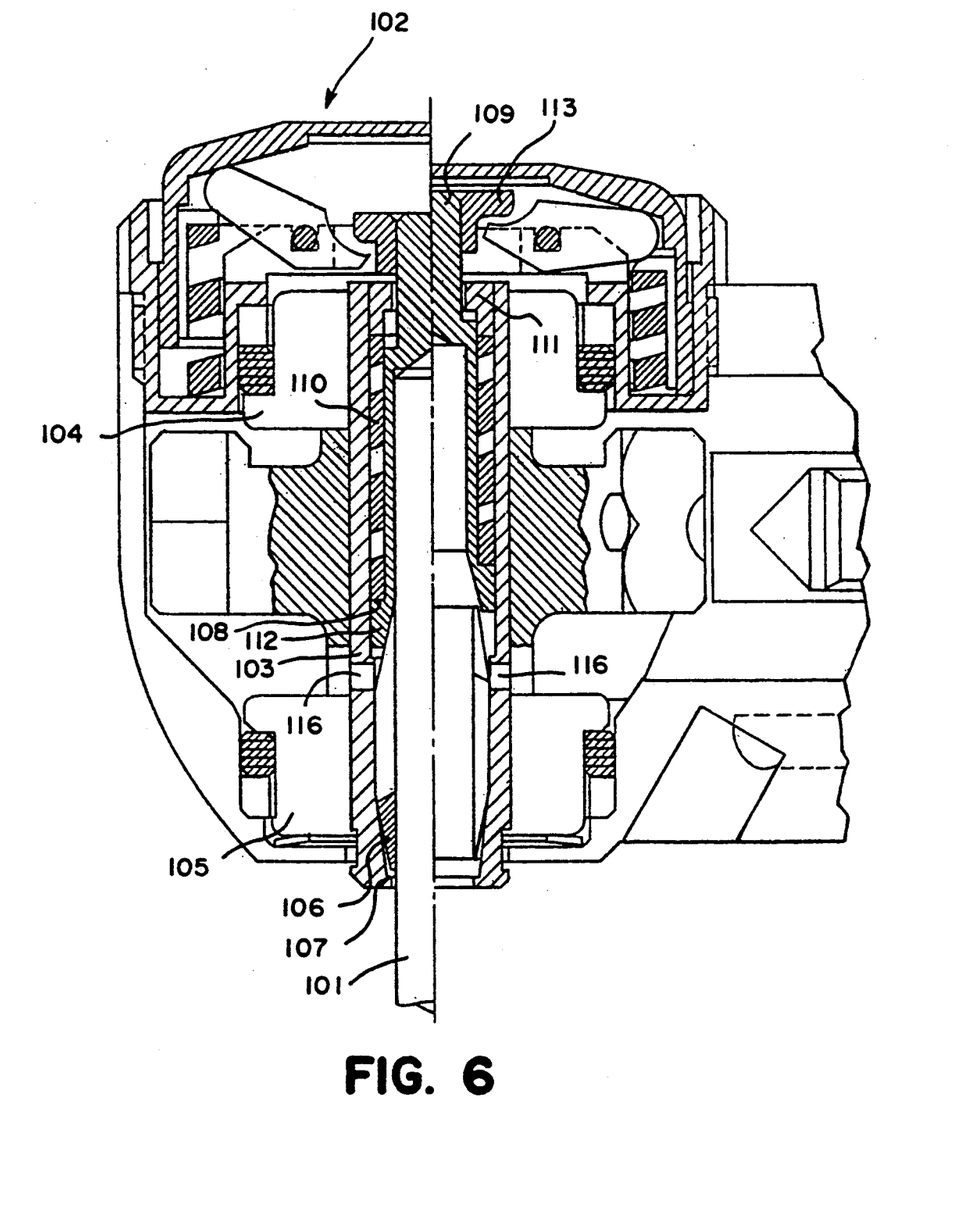
FIG. 6 is a variant, seen in cutaway view, of a handpiece head equipped with a clamping and unclamping device, respectively in the clamping position on the left-hand side and in the unclamping position on the right-hand side.

Reference is made to FIG. 6.

The shank (101) of a dentistry instrument is inserted in the head (102) of the handpiece essentially inside a cylindrical shaft (103) fixed in translation but movable in rotation by bearings (104, 105).

The shank (101) is held by at least one collet chuck (106) of general conical shape. The lower part of the chuck cooperates with a fixed ramp (107) of corresponding shape formed in the base of the shaft, on its inner face.

The upper part of the chuck cooperates with a ramp (108) movable in translation and formed on the front face of a pusher (109) movable in translation inside the shaft, and whose construction will be explained subsequently.

The collet chuck will be produced by partial longitudinal slitting of a hollow body of revolution. It will advantageously be symmetrical.

It would also be possible to provide the device with two chucks of this type, mounted in series one above the other.

The construction of the pusher (109) will now be described.

The latter is of general cylindrical shape.

It is movable in translation in the shaft and partially covers the shank (101) of the dental instrument. The displacement is effected counter to a pressure spring (110) which bears on the one hand in the upper part on a seat (111) integral with the shaft and on the other hand in the lower part on a base (112) integral with the pusher and forming a single piece with the latter.

This construction shows that the unclamping of the shank of the instrument, that is to say the freeing of the collet chuck, is achieved by means of a traction exerted on the pusher, which is completely original.

To this end, the upper part of the pusher emerging from the shaft is provided, for example, with a shoulder (113) added to the latter or forming a single piece with the pusher. A traction exerted on the shoulder drives the pusher upwards by compressing the spring (110) and thereby frees the collet chuck in order to permit disengagement of the instrument or positioning of one in the head of the handpiece.

The head will be provided with a device making it possible to convert the movement of displacement of the push-button of the head of the handpiece into a reverse movement of the pusher, identical to that described previously.

According to one implementation variant, the shaft is provided with bores (116) allowing the pressure possibly prevailing in the handpiece to establish itself inside the clamping device in order to prevent the penetration of pollutant elements or dirt.

According to another variant of implementation, the chuck will be single-collet chuck and will be monobloc with the pusher.

As an alternative to the structure of the chuck with a single-collet and monobloc with the pusher, it has also been considered useful to limit the deformation of the chuck when the latter is in the clamped position in the absence of an instrument shank, in order to prevent a permanent deformation of the clamping arms.

To this end, an alternative is proposed to the device for clamping and unclamping the shank of a dental instrument in the head of a dentistry handpiece, characterized in that the chuck is provided with an abutment cooperating with an associated shape of the shaft, in order to limit the travel of the chuck in the clamping direction.

Reference will be made to FIGS. 7 to 11.

Figure 7:
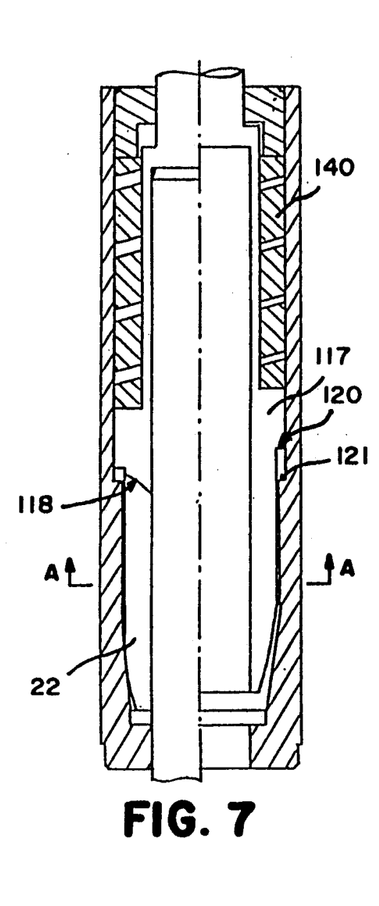
FIG. 7 is a variant of FIG. 6 showing a semi-cutaway view of a handpiece head equipped with the device, respectively in the clamping position on the left-hand side and in the unclamping position on the right-hand side, according to a second variant with a transverse cutaway along A—A in FIG. 7A.

Reference is made first of all to FIG. 7.

The collet chuck (117) is monobloc with the pusher. It is acted upon by an equilibrated machined spring (140) arranged concentric to the pusher around the latter.

Its length will preferably be a multiple of the pitch.

According to this alternative, the chuck comprises an annular abutment (120) which limits the load or the stress on the chuck in the case where there is no instrument shank introduced into the said chuck.

The abutment (120) cooperates with an annular shoulder (121) of corresponding shape in the shaft.

Figures 7A, 8, 8A, 9, 9A:
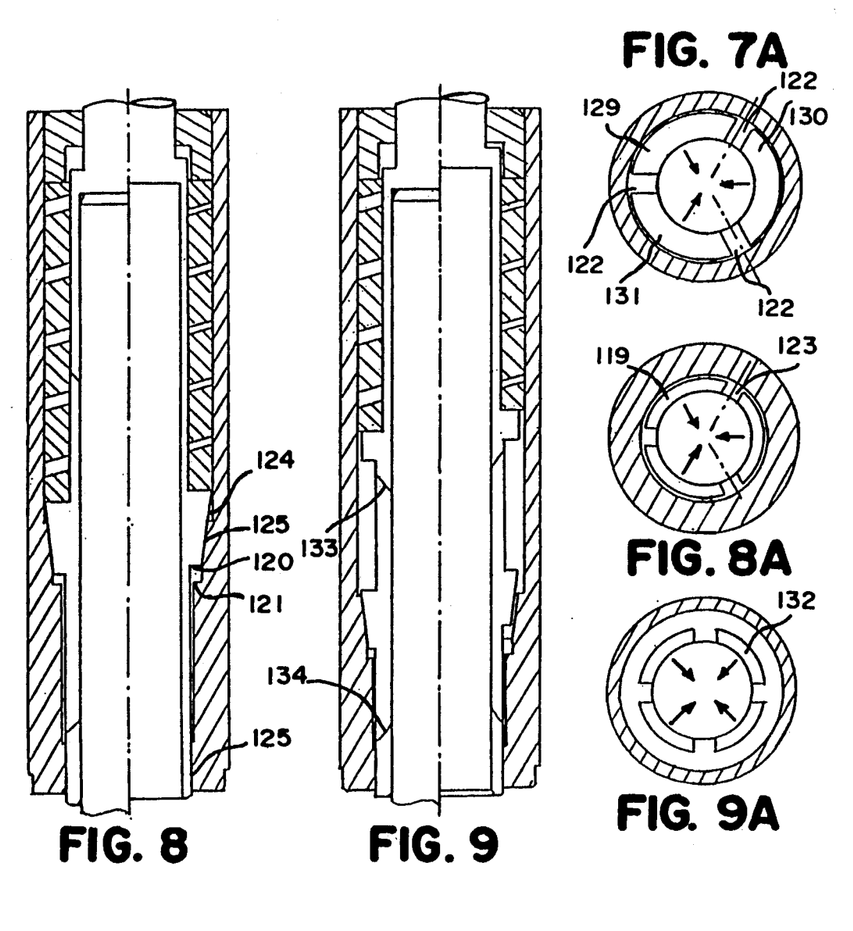

As emerges from the cutaway in FIG. 7A, the chuck is made up of, for example, three tongues (129, 130, 131) determining between them three longitudinal slits (122).

The clamping tongues are articulated at the upper limit of the axial slots at a point (118).

In this construction, the wedging of the end of the chuck on its seat is done away with due to the mobility of the chuck relative to its seat.

It can thus admit seats of low conicity, from which there results a more effective clamping.

The longitudinal slits in this variant open at the ends of the chuck, in particular when the chuck is a single asymmetrical chuck.

In the variant in FIGS. 8 and 8A, the slits (123) are formed in one part of the chuck, without opening out at the ends of the said chuck.

In this case it is provided, all other things being equal compared to the embodiment in FIG. 7, that the chuck is provided with a generally conical shape (124) situated in the middle part relative to the slits, the said conical shape (124) cooperating with an associated conical shape (125) in the shaft in order to ensure the clamping by deformation of the arms (119) defined by the slits (123).

In addition to the advantages of the preceding embodiment, it will be noted that the rod of the cutter cooperates only with a single piece of the handpiece.

The maximum clamping is situated at the middle of the tongues (at the level of the conical part).

The slots are formed as far as the part receiving the spring, in order to allow the tongues a more flexible flexion.

The embodiment in FIGS. 9 and 9A is similar to the preceding one, but with four tongues (132).

In these two embodiments, there are two points of articulation (133, 134) for the clamping tongues at the lower and upper limits of the axial slots.

The slots are limited as far as the spring, since the latter would occasion a stress on the tongues during unclamping; the removal of the cutter would then be disturbed by this.

Figure 10:
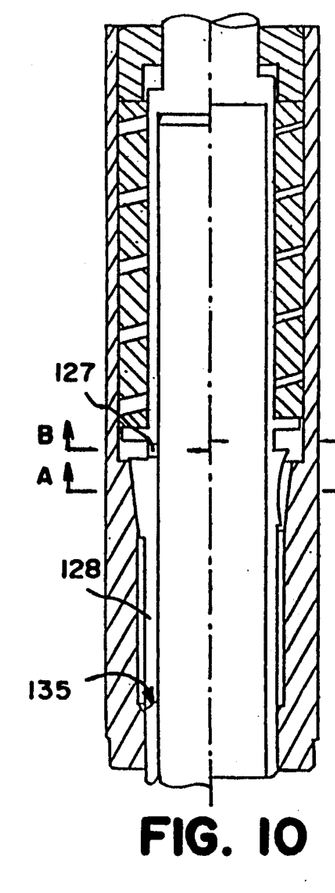
Figures 10A, 10B, 11:
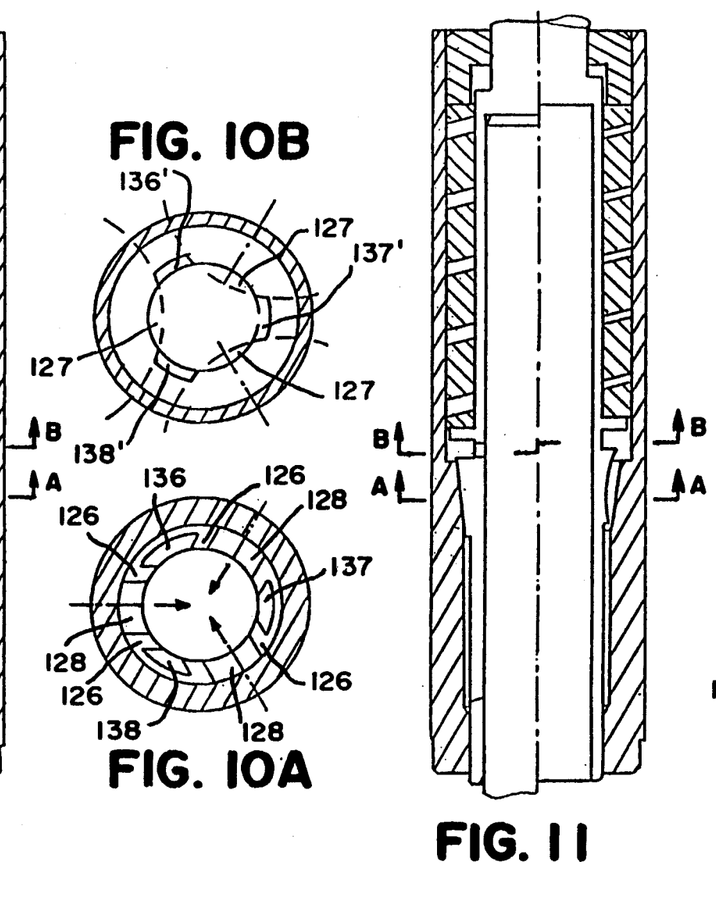

Reference will now be made to FIGS. 10 and 10A. In this embodiment, the slits (126) are formed in pairs and the slits of one pair are joined at one of their ends by a transverse split (127) relative to the axis chuck, thereby defining flexible arms (128). The conical shape of the chuck and the associated shape of the shaft can be judiciously placed near the yielding end of the flexible arms (128), the said conical shape of the chuck being limited at the level of the flexible arms by clearance between the said arms.

The point of articulation (135) of the tongues is situated at the lower limit of the axial slots. The chuck comprises cut-out fixed parts (136, 137, 138) and (136', 137',138').

The maximum clamping is situated at the level of the conical part of the tongues, which are free at one end and articulated by the point (135) at the other end.

Figure 11A:
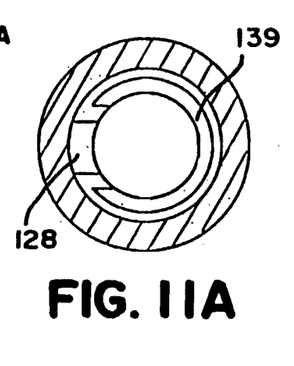
Figure 11B:
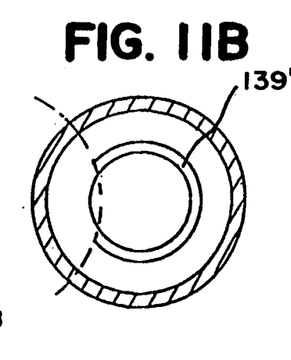

According to the alternative in FIGS. 11, 11A and 11B, of the same type as those in FIGS. 10, 10A and 10B, the clamping device comprises only one single yielding arm (128). The remainder of the chuck is a cut-out fixed part (139, 139').

In this case, the clamping is not concentric, but always forces the rod of the cutter against the face of the chuck opposite the tongue.

In the alternatives in FIGS. 8 to 11, the chuck is at the front end of the shaft sliding in a diameter (125) of the said shaft, in order to ensure a good centring of the chuck in the shaft, preventing unbalance.

Figure 12:
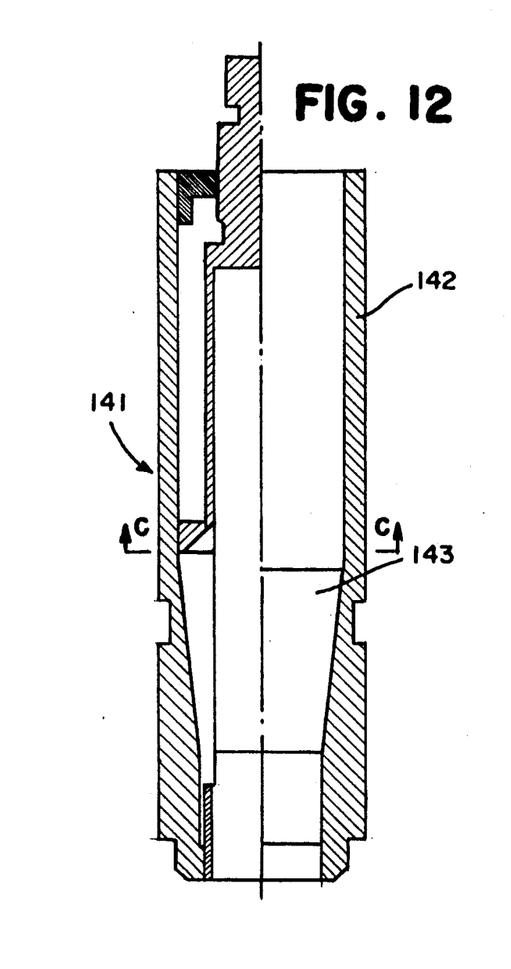
FIG. 12C is a view of FIG. 12 in cutaway C—C.
FIG. 12B is a view of FIG. 12C in cutaway B—B.
FIG. 12A is a view of FIG. 12C in cutaway A—A.

Reference will now be made to FIGS. 12 and following.

The clamping-unclamping assembly (141) consists of a shaft (142) comprising a conical part (143) in which there cooperate one or more shells (144, 145) (here two, diametrically opposed), lodged in a sheath (146) capable of being displaced axially by the action of a spring or the push-button An axial displacement of the sheath towards B (clamping action by means of the spring effect) results in a considerable radial component on the shells (as a function of the conicity) ensuring the clamping; an axial displacement of the sheath towards H (unclamping action by means of the effect on the push-button) releases the shells, ensuring unclamping. The directions B and H are shown in FIG. 12.

Figures 12A, 12B, 12C:
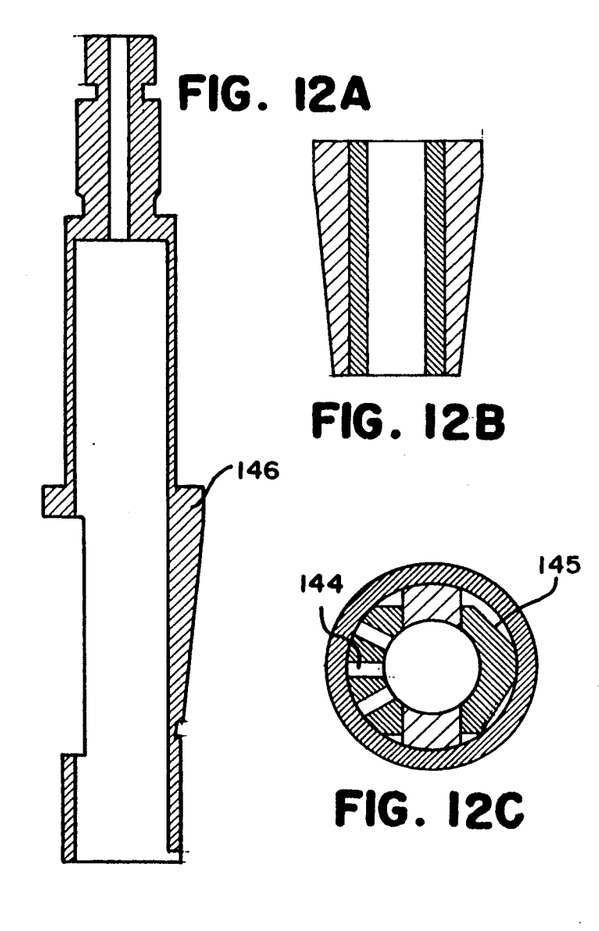

In order to guarantee the clamping of a cutter shank, there must be a play P between the sheath and the shells as shown in FIG. 12C. When the play is zero, the shells are bearing against the sheath. This position can then limit the minimum diameter of clamping (position without rod introduced into the sheath).

Figure 13:
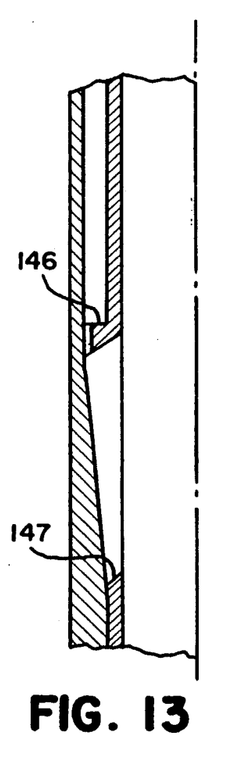
FIG. 13 is a variant, in cutaway view, of the clamping device inside the shaft.

In order to improve the efficacy of the clamping, it is possible to conceive various designs for the shells, for example: split in staggered formation, monobloc with cutting-out . . . It is also possible to conceive two inclined planes (146, 147) on the sheath and the shells, as illustrated in FIG. 13, favouring the radial component for clamping as for unclamping.

I claim:

1. A push-button control device for clamping and unclamping a cutting shank of a dentistry instrument in a head of a contra-angle or a handpiece, wherein displacement of the push-button is effected counter to a pressure spring, comprising:

at least one tilting lever-type reversal element for receiving moments responsive to pressure on the push-button and for converting said movements into a traction movement exerted by the reversal element on a pusher controlling a collet chuck for holding a neck formed in the shank of the instrument responsive to a helical pressure spring which bears at one end on a movable base and at another end on a seat;

wherein the head has a movable annular piece including a shoulder of the pusher, the annular piece being integral in translation with the movable base so that axial displacement of the movable base, the annular piece and the pusher operates the spring, thereby freeing or blocking the neck of the instrument which is held by the chuck;

wherein the axial displacement of the movable base, the annular piece and the pusher is controlled by the push-button, which is displaced counter to the spring in a release position; and wherein the push-button is interconnected with the movable base, the annular piece and the pusher by a link defined by at least one lever articulated on a pin and including a small arm for acting on the shoulder and a large arm coupled with the push-button on an inner face of the push-button.

2. The device of claim 1 which comprises a plurality of levers.

3. A push-button control device for clamping and unclamping a cutting shank of a dentistry instrument in a head of a contra-angle or a handpiece, wherein displacement of the push-button is effected counter to a pressure spring, comprising:

at least one tilting lever-type reversal element for receiving movements responsive to pressure on the push-button and for converting said movements into a traction movement exerted by the reversal element on a pusher controlling a collet chuck for holding a neck formed in the shank of the instrument responsive to a helical pressure spring which bears at one end on a movable base and at another end on a seat;

wherein the head has a movable annular piece including a shoulder of the pusher, the annular piece being integral in translation with the movable base so that axial displacement of the movable base, the annular piece and the pusher operates the spring, thereby freeing or blocking the neck of the instrument which is held by the chuck;

wherein the axial displacement of the movable base, the annular piece and the pusher is controlled by the push-button, which is displaced counter to the spring in a release position; and wherein the push-button is interconnected with the movable base, the annular piece and the pusher by a link defined by a small arm, a large arm and a fulcrum in the form of a ball, wherein the spring bears on the large arm, and the large arm is coupled with the push-button on an inner face of the push-button.

4. A push-button control device for clamping and unclamping a cutting shank of a dentistry instrument in a head of a contra-angle or a handpiece, wherein displacement of the push-button is effected counter to a pressure spring, comprising:

at least one tilting lever-type reversal element for receiving movements responsive to pressure on the push-button and for converting said movements into a traction movement exerted by the reversal element on a pusher controlling a collet chuck for holding a neck formed in the shank of the instrument responsive to a helical pressure spring which bears at one end on a movable base and at another end on a seat;

wherein the head has a movable annular piece including a shoulder of the pusher, the annular piece being integral in translation with the movable base so that axial displacement of the movable base, the annular piece and the pusher operates the spring, thereby freeing or blocking the neck of the instrument which is held by the chuck;

wherein the axial displacement of the movable base, the annular piece and the pusher is controlled by the push-button, which is displaced counter to the spring in a release position; and wherein the push-button is interconnected with the movable base, the annular piece and the pusher by a link defined by a boat-type lever including a basin for receiving a roller ball, and extended by an arm ensuring off-center contact relative to the axis of rotation of the lever.

5. A push-button control device for clamping and unclamping a cutting shank of a dentistry instrument in a head of a contra-angle or a handpiece, wherein displacement of the push-button is effected counter to a pressure spring, comprising:

at least one tilting lever-type reversal element for receiving movements responsive to pressure on the push-button and for converting said movements into a traction movement exerted by the reversal element on a pusher controlling a collet chuck for holding a neck formed in the shank of the instrument responsive to a helical pressure spring which bears at one end on a movable base and at another end on a seat;

wherein the head has a movable annular piece including a shoulder of the pusher, the annular piece being integral in translation with the movable base so that axial displacement of the movable base, the annular piece and the pusher operates the spring, thereby freeing or blocking the neck of the instrument which is held by the chuck;

wherein the axial displacement of the movable base, the annular piece and the pusher is controlled by the push-button, which is displaced counter to the spring in a release position; and wherein the push-button is interconnected with the movable base, the annular piece and the pusher by a link defined by a balance-arm type lever having a fulcrum formed as a boss on a cooperating support piece.

6. A push-button control device for clamping and unclamping a cutting shank of a dentistry instrument in a head of a contra-angle or a handpiece, wherein displacement of the push-button is effected counter to a pressure spring, comprising:

at least one reversal element for receiving movements responsive to pressure on the push-button and for converting said movements into a traction movement exerted by the reversal element on a pusher controlling a collet chuck for holding a neck formed in the shank of the instrument, wherein said reversal element includes a plurality of balls operated upon by a ramp of the push-button in contact with a counter-ramp of a ring controlling a shoulder formed in the pusher, for displacing the balls toward a corresponding seat.

7. The device of claim 6 wherein the collet chuck includes an actuating ramp of corresponding shape and integral with the pusher, wherein the collet chuck is movable in translation inside a shaft, wherein displacement of the pusher is controlled by the push-button, and wherein the pressure spring bears at one end on a base integral with the pusher and at another end on a fixed seat integral with the shaft.

8. The device of claim 7 wherein clamping forces of the collet chuck increase with forces of the traction movement.

9. The device of claim 7 wherein the collet chuck is of a generally conical form, having a lower part which cooperates with a fixed ramp of corresponding shape formed in base portions of the shaft, on an inner face thereof.

10. The device of claim 7 wherein the collet chuck is formed with partial longitudinal slits in a hollow body of revolution.

11. The device of claim 10 wherein the collet chuck is symmetrical.

12. The device of claim 7 wherein the pusher is generally cylindrical in shape, and is movable in translation relative to the shaft, for partially covering the shank of the dental instrument.

13. The device of claim 12 wherein said transaction is counter to the pressure spring, which bears at an upper end on a seat integral with the shaft and at a lower end on a base forming a single piece and integral with the pusher.

14. The device of claim 7 wherein upper portions of the pusher emerging from the shaft are provided with a shoulder so that a traction movement exerted on the shoulder drives the pusher upward by compressing the spring, thereby freeing the collet chuck for interaction with the instrument.

15. The device of claim 7 wherein the shaft includes a plurality of bores for passing pressure prevailing in the handpiece inside the clamping device, to prevent a penetration of pollutant elements or dirt.

16. The device of claim 7 wherein the chuck is a single-collet chuck, monobloc with the pusher.

17. The device of claim 16 wherein the collet chuck includes an abutment which cooperates with an associated shape on the shaft to limit travel of the chuck during clamping.

18. The device of claim 17 wherein the collet chuck is monobloc with the pusher, and is acted upon by an equalizing machined spring arranged concentric with the pusher.

19. The device of claim 18 wherein the collet chuck has a length and a pitch, and wherein the length is a multiple of the pitch.

20. The device of claim 17 wherein the shape on the shaft is an annular shoulder.

21. The device of claim 17 wherein the collet chuck is comprised of three tongues defining three longitudinal slits which open out at ends of the chuck, and wherein the tongues are articulated at an upper limit of the slits.

22. The device of claim 17 wherein arm-defining slits are formed on one part of the chuck, which open out in a portion for receiving the spring, wherein the chuck is provided with a generally conical shape located in mid-portions of the chuck relative to the slits, and wherein the conical shape cooperates with an associated conical shape formed in the shaft to ensure clamping by deformation of the arms defined by the slits.

23. The device of claim 22 wherein the collet chuck is comprised of four tongues.

24. The device of claim 22 wherein the collet chuck incorporates two points of articulation for the clamping tongues, at lower and upper limits of the axial slots.

25. The device of claim 17 having paired slits, one pair of slits being joined at one end by a transverse slit relative to the axis of the chuck, thereby defining flexible arms, so that the conical shape of the chuck and the associated shape of the shaft are placed near a yielding end of the flexible arms.

26. The device of claim 25 wherein the conical shape of the chuck is limited at the level of the flexible arms by a clearance between the arms so that a point of articulation of the tongues is situated at a lower limit of the axial slots and so that the chuck comprises cut-out fixed parts.

27. The device of claim 17 wherein the collet chuck is comprised of a single yielding arm, with a remainder of the chuck being a cut-out fixed part.

28. The device of claim 17 wherein the collet chuck slides in a bore of the shaft.

29. The device of claim 17 wherein the collet chuck includes a shaft having a conical part for receiving at least one shell lodged in a sheath for axial displacement responsive to the push-button.

30. The device of claim 29 wherein a play is left between the sheath and the shell.

31. The device of claim 29 wherein the shell is slit in a staggered formation.

32. The device of claim 29 wherein the shell is a cut-out.

33. The device of claim 29 having two inclined planes on the sheath and two inclined planes on the shell.

* * * * *